(12) United States Patent
Kumar et al.

(10) Patent No.: US 7,345,071 B2
(45) Date of Patent: *Mar. 18, 2008

(54) PROCESS FOR THE SYNTHESIS OF LOSARTAN POTASSIUM

(75) Inventors: Ashok Kumar, Mumbai (IN); Rajesh Kumar Keshava Prasad Singh, Mumbai (IN); Nalinakshya Balaram Panda, Mumbai (IN); Abhay Atmaram Upare, Mumbai (IN); Manmohan Madhavrao Nimbalkar, Mumbai (IN); Satish Rajanikant Soudagar, Mumbai (IN); Ashvini Kumar Nand Kishore Saxena, Ratlam (IN)

(73) Assignee: IPCA Laboratories Limited (IN)

( * ) Notice: Subject to any disclaimer, the term of this patent is extended or adjusted under 35 U.S.C. 154(b) by 14 days.

This patent is subject to a terminal disclaimer.

(21) Appl. No.: 10/913,121

(22) Filed: Aug. 5, 2004

(65) Prior Publication Data

US 2005/0070586 A1    Mar. 31, 2005

Related U.S. Application Data

(63) Continuation-in-part of application No. 10/714,724, filed on Nov. 17, 2003, now Pat. No. 6,953,856.

(51) Int. Cl.
*A61K 31/41* (2006.01)
*C07D 257/04* (2006.01)

(52) U.S. Cl. ...................... 514/381; 548/252

(58) Field of Classification Search ............... 549/252; 514/381
See application file for complete search history.

(56) References Cited

U.S. PATENT DOCUMENTS

| | | | |
|---|---|---|---|
| 5,138,069 | A | 8/1992 | Carini et al. |
| 5,281,603 | A | 1/1994 | Venkatesan et al. |
| 5,281,604 | A | 1/1994 | Levin et al. |
| 5,608,075 | A | 3/1997 | Campbell, Jr. et al. |

FOREIGN PATENT DOCUMENTS

| | | |
|---|---|---|
| WO | WO 93/10106 | 5/1993 |
| WO | WO 95/17396 | 6/1995 |
| WO | WO 98/18787 | 5/1998 |
| WO | WO 01/81336 | 11/2001 |
| WO | WO 02/094816 | 11/2002 |
| WO | WO 03/048135 | 6/2003 |
| WO | WO 03/093262 | 11/2003 |

OTHER PUBLICATIONS

Burrell, Drug Safety, (1997), vol. 16(1), pp. 56-65.*

* cited by examiner

*Primary Examiner*—Taofiq Solola
(74) *Attorney, Agent, or Firm*—Blank Rome LLP

(57) ABSTRACT

Improved processes using primary, secondary and tertiary alcohols and with safer mode of introduction of the reagent and reaction conditions are described. Further, the process of manufacture of Losartan potassium by use of alkali metal salt such as Potassium carbonate is disclosed. A process for preparation of the polymorphic Form I of Losartan potassium is also disclosed herein.

13 Claims, 6 Drawing Sheets

PROCESS FOR THE SYNTHESIS OF LOSARTAN POTASSIUM

RELATED APPLICATIONS

This application is a continuation-in-part of U.S. application Ser. No. 10/714,724, filed 17 Nov. 2003, now U.S. Pat. No. 6,953,856.

RELATED APPLICATIONS

This application is related to our earlier PCT application No. PCT/IN03/00230. This application claims priority from Indian National patent Application serial no. 14/MUM/2004, filed on 6 Jan. 2004.

TECHNICAL FIELD

This invention relates to improvement in process for preparation of Losartan Potassium as claimed in our main application. More specifically this invention relates to a commercial process for preparation of the polymorphic Form I of Losartan potassium and an improvement in use of reagent in the reaction and conditions thereof for the preparation of the said Losartan Potassium as claimed in our main application as above.

BACKGROUND AND PRIOR ART

Among cardiovascular drugs, Angiotensin II receptor antagonists like Losartan potassium are prominently used as an active ingredient in the management of hypertension. Losartan potassium plays an effective role in patients having difficulty in tolerating ACE inhibitors. The chemical name of Losartan potassium is 2-n-Butyl-4-Chloro-1-[((2'-tetrazol-5-yl)-1,1'-bisphenyl-4-yl)methyl]-imidazole-5-methanol potassium.

It is known in the art to synthesize Losartan potassium from the acid form of Losartan. Losartan potassium (shown as the compound of Formula (I) below) is known in the art is synthesized by reacting its acid (shown as the compound of formula (II) below) with KOH. The intermediate acid Formula (II) in turn is synthesized by detritylation of 2-n-butyl-4-chloro-5-hydroxymethyl-1-[((2'-triphenylmethyltetrazole-5-yl)biphenyl-4-yl) methyl] imidazole (shown as the compound of Formula (III) below)

The synthesis of Trityl Losartan (the reactant of Formula (III) below) is known in the art. See 34 J. MED. CHEM. 2525-27 (1991); 59 J. ORG. CHEM. 6391-94 (1994); U.S. Pat. No. 5,138,069. Trityl Losartan (and the Losartan acid/free Losartan) and may alternatively be prepared using the reactions and techniques described in U.S. Pat. No. 5,138,069 and patent application number WO93/10106.

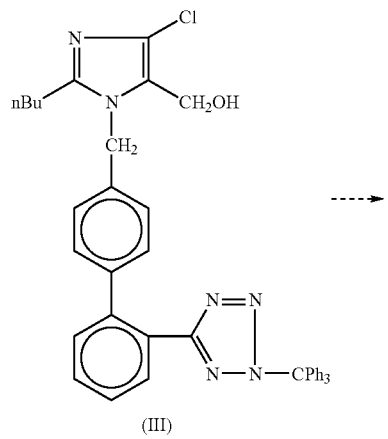

(III)

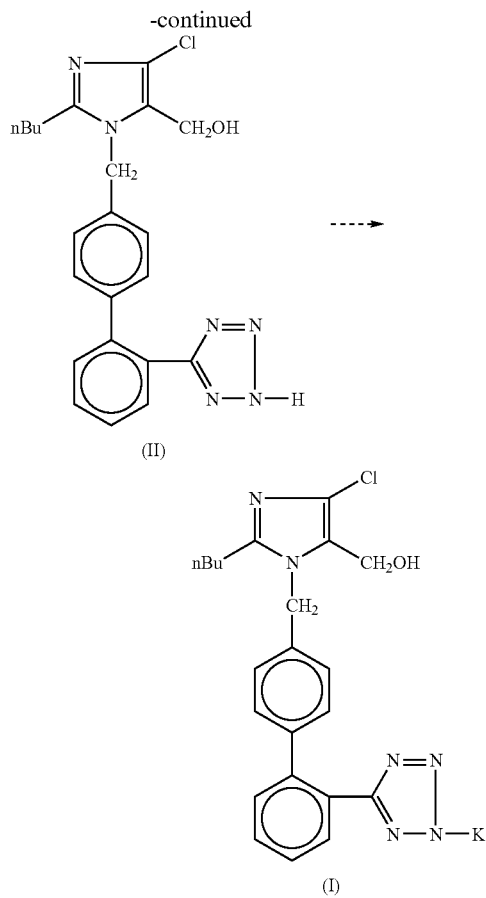

The preparation from Trityl Losartan (the reactant of Formula (III) of Losartan acid (II) by acid-catalyzed cleavage of trityl group from Trityl Losartan (III) is disclosed in U.S. Pat. No. 5,281,603. Another method disclosed to prepare Losartan acid from trityl losartan is disclosed in U.S. Pat. No. 5,281,604. In this process Trityl Losartan (III) is refluxed in a mixture of methanol and tetrahydrofuran in presence of catalytic acid like hydrochloric acid for 18 hours to get Losartan acid (II).

Patent application number WO98/18787 describes a method, which also starts with a solution of Losartan Potassium (I) in aqueous isopropyl alcohol and is heated to distill out water-isopropyl alcohol mixture to lower the water content to 2.6%. Further excessive seeding is carried out with slurry of Losartan Potassium (I) in cyclohexane until the seed remains undissolved. The Precipitation of the product is then achieved by continuous distillation of ternary azeotrope with simultaneous addition of cyclohexane to the reaction mass. This azeotrope distillation is carried out until moisture level decreases to about 0.2 to 0.11%. The crystallized product thus obtained is filtered.

The present invention avoids the use of stringent azeotropic distillation of water from the reaction mass to precipitate Losartan potassium. Also it avoids the use of antisolvents for the removal of water or for the precipitation of Losartan poatassium as taught by the prior art.

Similarly, in patent application number WO01/81336, Richter Gedeon describes treatment of Trityl Losartan (III) with potassium hydroxide in primary alcohols and crystallization of the product (I) from methanol with the help of anti solvents such as dipolar aprotic solvent (acetonitrille), aprotic solvent (straight or branded chain or cyclic aliphatic hydrocarbons) or a protic solvent (sec. butanol).

The Richter Gedeon approach was found to be easy and superior to the existing methods, however was found to suffer from various drawbacks as summarized below:

a) The product obtained does not pass desired solubility in various solvents. To make the product improve in quality, it needs an extra purification as per the Richter Gedeon application.

b) Purification step in the process, the resultant purity and the yields thereof, depends on very precise ratios of solvent mixture (e.g. methanol, cyclohexane or acetonitrile).

c) High volume of solvents and that too in very precise combination in purification which leads to capacity reduction of plant production/facilities.

d) Recovery and recyclability of the solvents (methanol and anti solvents) from its mixture is difficult and needs careful purification by distillation to get recyclable solvents, with very little value addition. The non-recovery option, on the other hand, leads to high pollution load.

Patent application number WO 02/094816, discloses use of acetone, ethyl acetate, acetonitrile and toluene as anti-solvents and has similar problems of recovery and reuse of solvents and high cost of production. Since isolation of the product is simply by precipitation using anti solvents, the product needs further purification to pass the required tests, in this case also.

The art not only teaches the need for purifying the resulting Losartan potassium (I), but also various methods to purify it. For example U.S. Pat. No. 5,608,075 discloses two polymorphic forms of Losartan Potassium, which are Form I and form II. Their method of preparation and characterization by X-ray powder diffraction pattern, DSC thermograms, FT-IR spectra, Raman spectra and $C^{13}$ NMR (solid state) spectra were also given. The disclosed procedure for polymorphic Form I is the addition of aqueous solution of (I) to a refluxing mixture of cyclohexane and isopropyl alcohol followed by azeotropically distilling out cyclohexane/isopropyl alcohol/water ternary azeotrope at 64° C. while the Form I crystallizes out at 69° C.

Our unpublished U.S. patent application Ser. No. 60/468, 208 having priority from Indian patent application serial No. 335/MUM/2003, filed on 03 Apr. 2003, addresses these problems by the use of potassium tertiary butoxide in alcoholic solvents for the detritylation and simultaneous formation of Losartan potassium. Moreover the invention discloses the isolation in a single solvent and the easy removal of triphenyl methyl methyl ether which gives high quality Losartan potassium after normal workup. The Losartan potassium produced by this process is found identical with the crystal structure set for polymorph Form I as complied with X-ray diffraction studies, Infrared Spectroscopy and Differential Scanning Calorimeter.

However it was desired to develop a process which can be more operator friendly. In our earlier patent application potassium tertiary butoxide in powder form is used, which has its disadvantages in handling on large scale in an inert nitrogen atmospheric condition. This has led us to improve the process as per the present invention. The present invention is intended to solve the problems associated with the handling of potassium tertiary butoxide in powder form. Further to that it is also of interest to substitute potassium tertiary butoxide by other reagents and to obtain specific polymorphic Form I of Losartan potassium.

SUMMARY OF INVENTION

Improved process using primary, secondary and tertiary alcohols with modified mode of employing of the reagent and reaction conditions is described. Process of manufacture of Losartan Potassium by user friendly reactants such as potassium tertiary butoxide solution in alcoholic solvents such as tertiary butanol or by substituting potassium tertiary butoxide by cheaper and milder potassium salts like anhydrous potassium carbonate or potassium bicarbonate as the detritylating agent and isolating Losartan potassium in its polymorphic Form I are disclosed.

DETAILED DESCRIPTION

Figure 1:
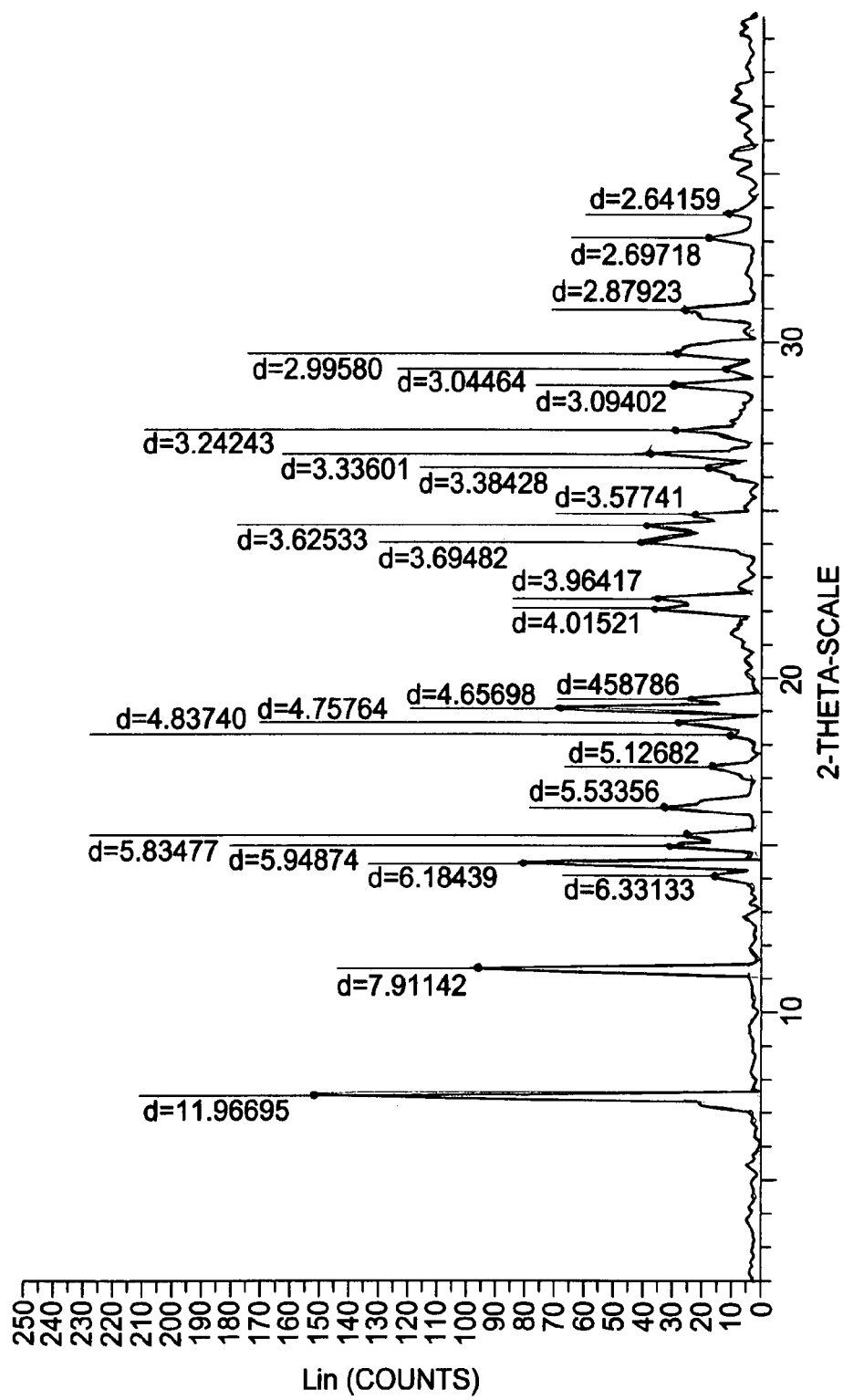
FIG. 1. Powder X-Ray Diffraction (PXRD) pattern of Losartan potassium Form I produced from Tetrahydrofuran as solvent.
Figure 2:
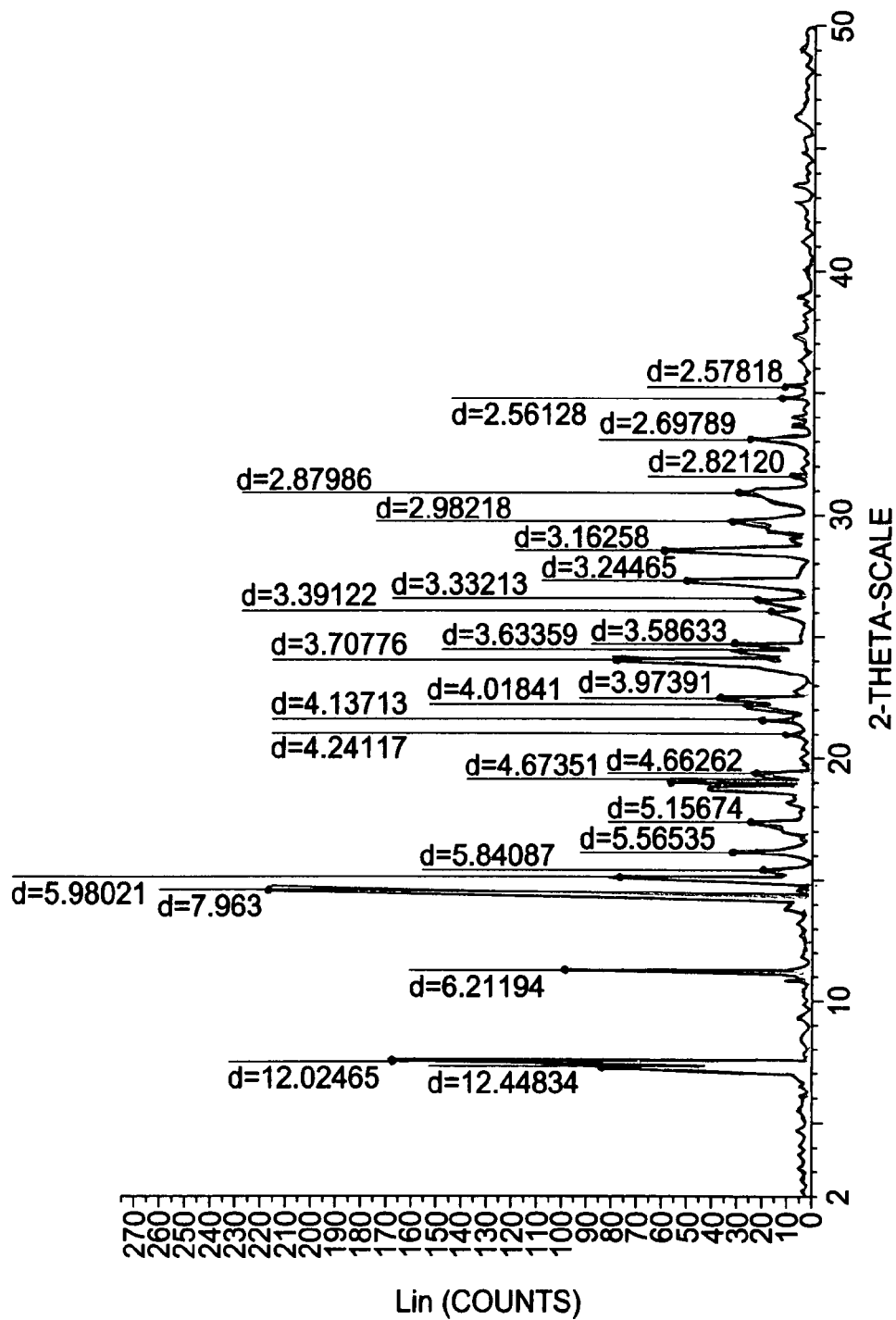
FIG. 2. Powder X-Ray Diffraction (PXRD) pattern of Losartan potassium Form I produced from Isopropyl alcohol as solvent.
Figure 3:
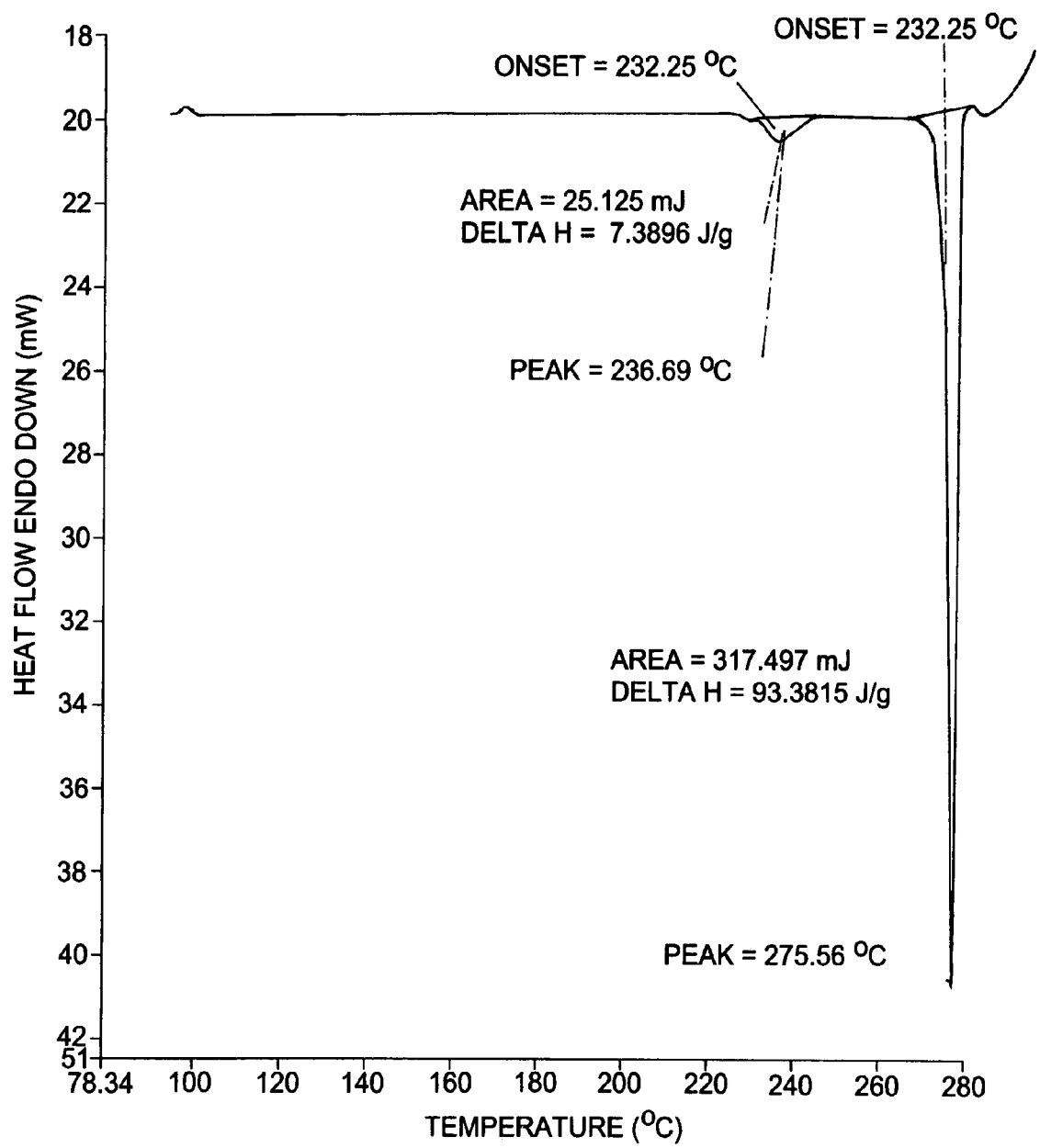
FIG. 3. Differential Scanning Calorimeter (DSC) thermogram of Losartan potassium Form I produced from Tetrahydrofuran as solvent.
Figure 4:
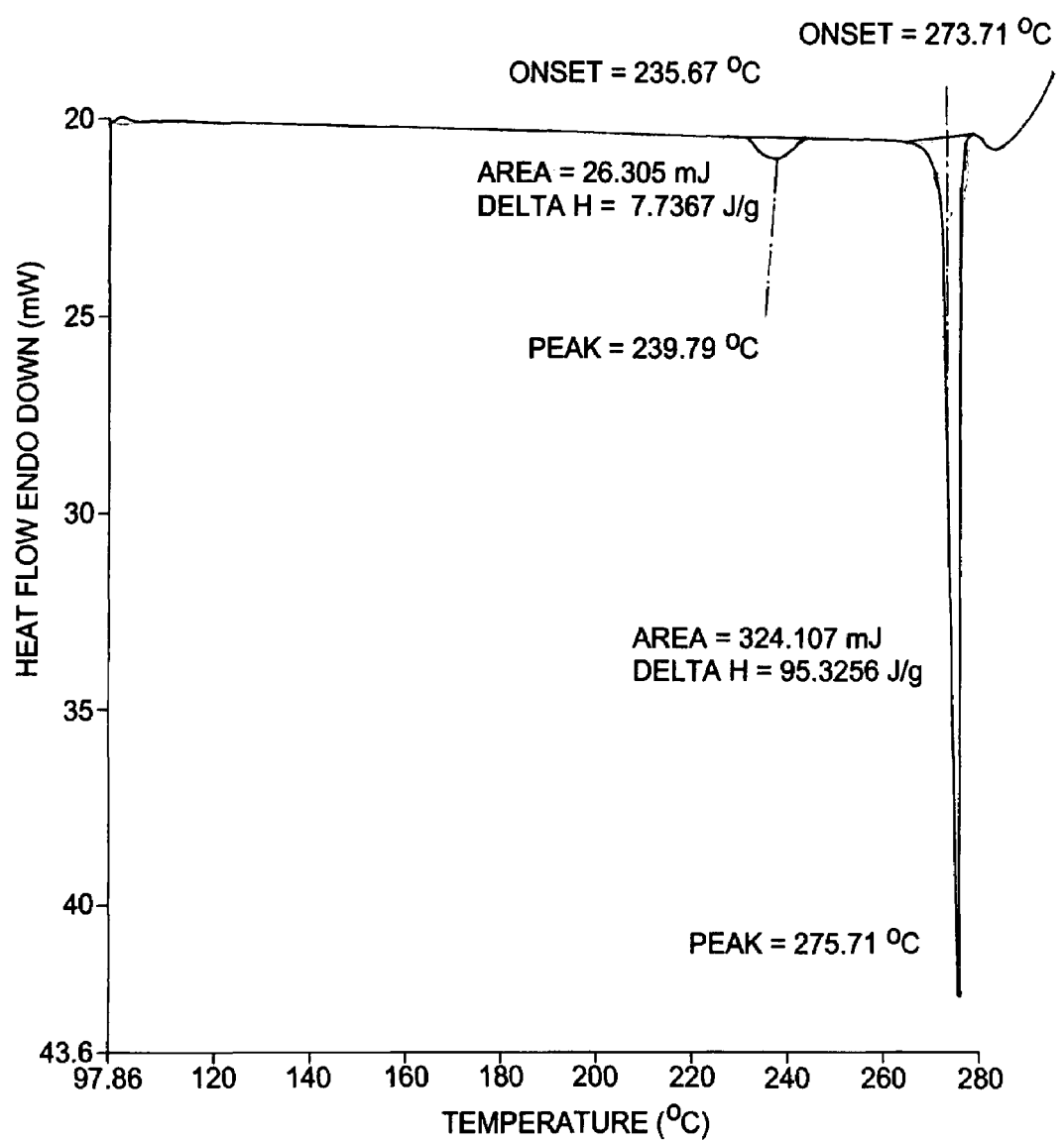
FIG. 4. Differential Scanning Calorimeter (DSC) thermogram of Losartan potassium Form I produced from Isopropyl alcohol as solvent.
Figure 5:
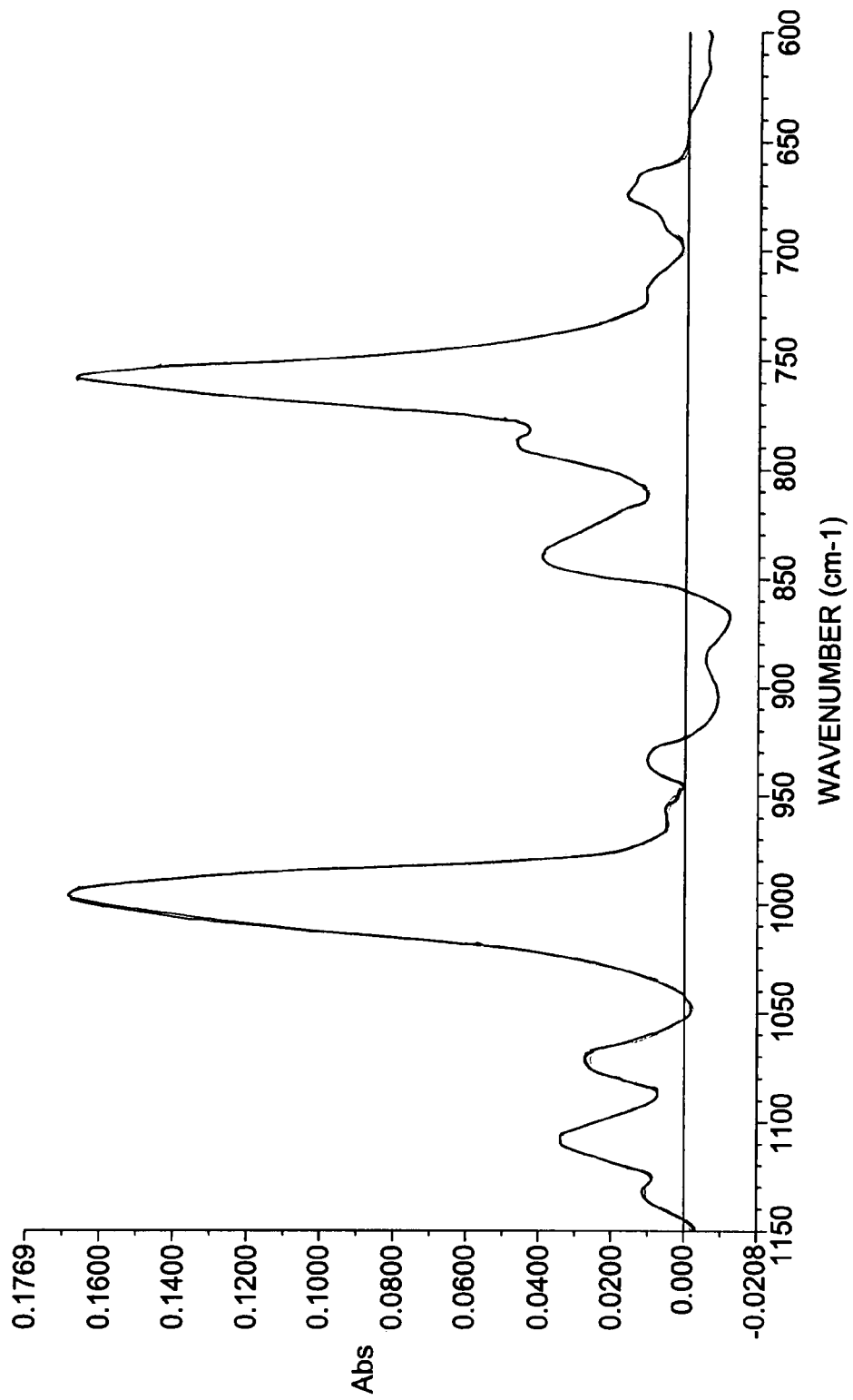
FIG. 5. FTIR spectrum of Losartan potassium Form I produced from Tetrahydrofuran as solvent from 1150 $cm^{-1}$ to 600 $cm^{-1}$.
Figure 6:
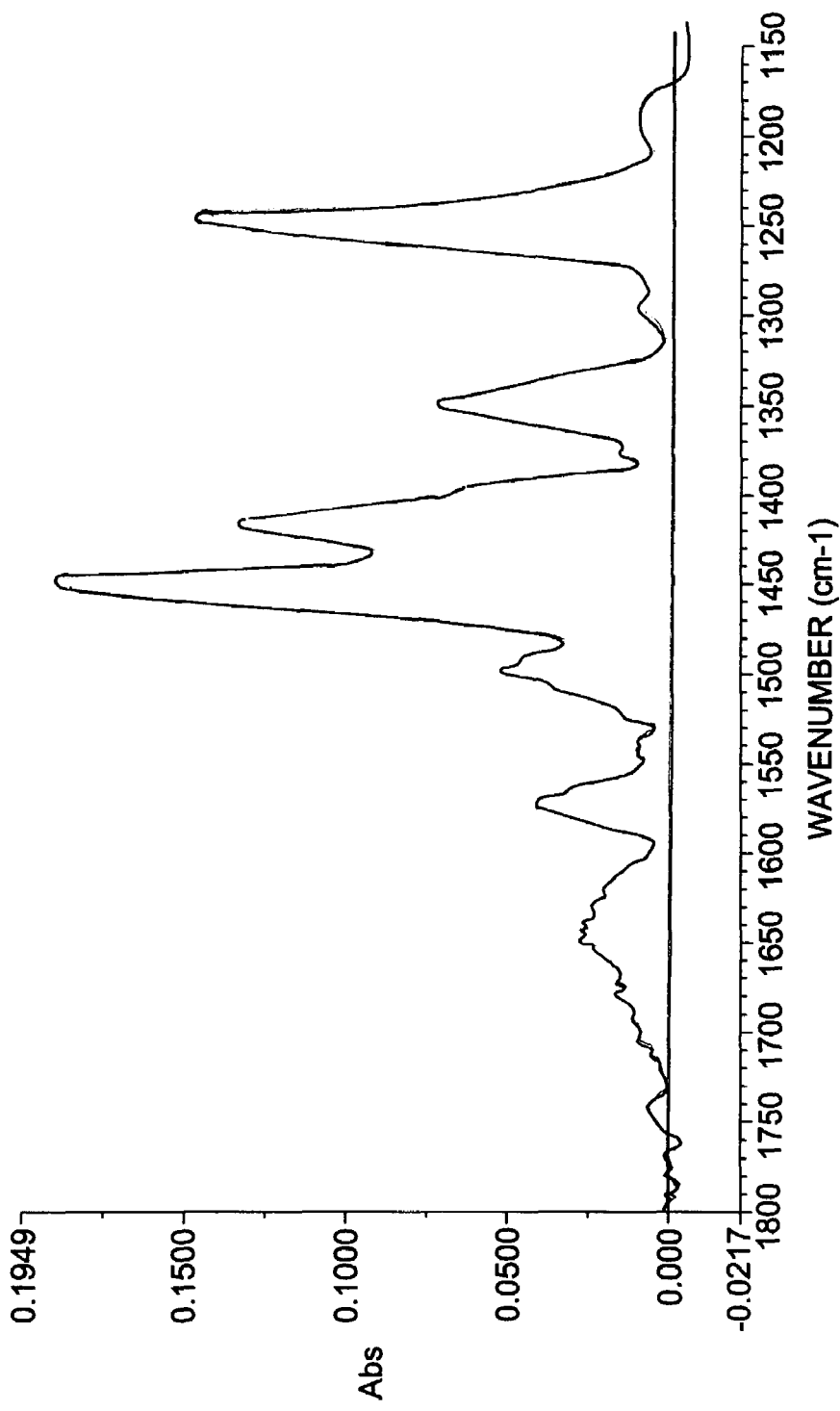
FIG. 6. FTIR spectrum of Losartan potassium Form I produced from Tetrahydrofuran as solvent from 1800 $cm^{-1}$ to 1150 $cm^{-1}$.

The present invention relates to an improvement in the user friendly use of the reagent in reaction and the reaction conditions for the preparation of Losartan Potassium as claimed in our main application as mentioned above. Additionally it provides process for preparation of polymorphic Form I of Losartan potassium.

The primary reagent in this invention is potassium tertiary butoxide, which is hygroscopic, air sensitive and a fluffy powder. To avoid contact with moisture, the operation using pure dry potassium tertiary butoxide needs to be carried out under nitrogen atmosphere. Handling of potassium tertiary butoxide on large scale in powder form may lead to flying of the reagent and is dangerous to the operating personnel. These problems of handling can be overcome by using Potassium tertiary butoxide in solution form as the reagent.

The improved process for preparation of Losartan Potassium by reacting, in primary alcohol such as methanol, a solution of Potassium tertiary butoxide in tertiary butanol with equimolar quantities of Trityl Losartan is disclosed.

In another embodiment, a solution of potassium tertiary butoxide in isopropyl alcohol is reacted in methanol with Trityl Losartan.

Also Potassium tertiary butoxide is used as a solution in secondary or tertiary alcohol.

A process for the synthesis of Losartan Potassium comprising reacting approximately equimolar quantities of Potassium salts such as potassium tertiary butoxide as a solution in a secondary/tertiary alcohol with Trityl Losartan in methanol; refluxing the reaction mixture to obtain a reaction mass comprising Losartan Potassium; monitoring the completion of reaction using TLC; concentrating the reaction mass to approximately 50%; cooling the reaction mass to approximately −5° C.; distilling out the methanol from the reaction mixture; stripping of methanol from the reaction mixture using solvents like isopropyl alcohol or tetrahydrofuran; maintaining the reaction mass in said solvent for approximately 12 hours at 25 to 30° C.; cooling the reaction mixture to 0-5° C.; filtering out Losartan potassium; washing with chilled Isopropyl alcohol and drying the Losartan Potassium under vacuum.

The secondary or tertiary alcohol used for the preparation of potassium tertiary butoxide solution is isopropyl alcohol and tertiary butanol.

The preferred strength of the potassium tertiary butoxide solution is 15 to 25% (w/v); most preferred strength is 15 to 20% (w/v).

Further it is also of interest to replace the potassium tertiary butoxide with other cheaper and safer potassium salts. This leads the other embodiment of the present invention wherein weaker bases like potassium carbonate have been used instead of stronger bases such as potassium hydroxide or potassium tertiary butoxide. In all the prior art strong bases viz. KOH are reported for the detrytilation of trityl Losartan. This is the first time reported here that weaker base such as potassium carbonate or potassium bicarbonate are used for the detryliation reaction.

In accordance with the present invention, potassium salts, such as anhydrous potassium carbonate in a primary or secondary alcohol, is reacted with Trityl Losartan to yield Losartan Potassium in high yields.

A process for manufacture of Losartan potassium comprising reacting equimolar quantities of anhydrous alkali metal salt in methanol with approximately 1 mole Trityl Losartan; refluxing the reaction mixture for 10 to 15 hours; monitoring the completion of reaction using TLC; concentrating the reaction mass to approximately 50%; cooling the reaction mass to approximately −5° C.; distilling out the methanol from the reaction mixture; stripping of methanol from the reaction mixture using solvents like isopropyl alcohol or tetrahydrofuran; maintaining the reaction mass in said solvent for approximately 12 hours at 25 to 30° C.; cooling the reaction mixture to 0-5° C.; filtering out Losartan potassium; washing with chilled Isopropyl alcohol and drying the Losartan Potassium under vacuum.

These potassium salts used are selected from anhydrous potassium carbonate and potassium bicarbonate. The primary or secondary alcohols used in the invention as the reaction media includes methanol, ethanol and isopropyl alcohol. This process of replacing potassium tertiary butoxide with these potassium salts has substantial advantages in terms of cost on a manufacturing scale.

Surprisingly it was found that if the suspension of Losartan potassium in isopropyl alcohol, obtained by deprotection of trityl Losartan, kept at a temperature of 25-30 degree for a period of 6-13 hours preferably 12 hours and is cooled slowly to a temperature of 0-5° C. in 2-12 hours, then the precipitated and dried crystals isolated in 82-92% yield are identical with the polymorphic Form I of Losartan potassium. The crystal form was found to be identical with the Polymorph Form I disclosed in the patent U.S. Pat. No. 5,608,075 by differential scanning calorimetry and X-Ray powder diffraction patterns studies.

In another embodiment of the present invention the Losartan potassium obtained after removal of triphenyl methyl ether was concentrated and the solvent is chased using solvent such as tetrahydrofuran (THF) or a mixture thereof with IPA. The THF layer was refluxed for a period of 0.5-3 hours followed by cooling of the solution to a temperature of 25-30° C. and kept at this condition for a period of 10-15 hours. The reaction mass was then chilled to a temperature of 0-5° C. There after the precipitated crystals filtered and dried, the crystals are identical with the polymorphic Form I of Losartan potassium. The crystal form was identified by differential scanning calorimetry and X-Ray powder diffraction patterns.

In another process variant of the invention the polymorph Form I was prepared by the following steps comprising reacting Trityl Losartan with equimolar quantity of anhydrous potassium carbonate in methanol; refluxing the resultant mixture for a period of 7-12 hours; concentrating methanol to half volume; filtering triphenyl methyl methyl ether; concentrating the methanol mixture to 50% volume; removing residual solvent using solvents like isopropyl alcohol, tetrahydrofuran (THF) or its mixture thereof and keeping the mass at 25-30° C. for aging the crystal growth for a period of 10-15 hours; chilling the said solvent layer to a temperature of 0-5° C. to precipitate the crystals of polymorph I and filtering the said precipitated crystals of polymorph Form I.

In other embodiment, the process for manufacture of polymorph Form I of Losartan potassium comprising suspending Losartan potassium obtained after detrytilation, in solvent tetrahydrofuran or its mixture thereof with solvents such as isopropyl alcohol at reflux; cooling to a temperature of 25-30° C.; aging the crystal at this temperature for a period of 7-13 hours and cooling the mass to a temperature of 0-5° C.

Preferably, tetrahydrofuran is used to suspend Losartan potassium obtained after detrytilation in the said manufacturing process of Polymorph Form I of Losartan potassium.

In another process variant Losartan potassium polymorph Form I was obtained by changing the base to potassium tertiary butoxide in place of potassium carbonate.

The following non-limiting examples further illustrate the best mode of carrying out the invention.

EXAMPLE 1

Under nitrogen atmosphere in a 2.0 liter flask, 150 ml. (16.70% w/v, 0.225 mole) solution of potassium tertiary butoxide in tertiary butanol is charged in methanol (725 ml). To this solution, 150 gm. of Trityl Losartan (0.225 mole) is added. The mixture is refluxed for 9 hours. The completion of reaction is monitored on TLC. After satisfactory completion, the reaction mass is concentrated to 50% and cooled to approximately −5° C. The reaction mass is filtered to separate the by-product from the reaction. After charcoalization of the filtrate, it is filtered through celite. Residual methanol is distilled out completely and stripped out using isopropyl alcohol (75 ml. each) twice. Isopropyl alcohol (225 ml.) is charged, reflux for 1 hour, cooled and kept for 12 hours at 25-30° C.

The reaction mass is then cooled to 0-5° C. and filtered. The resulting product, Losartan Potassium is then washed with chilled isopropyl alcohol (45 ml). The final product is dried at 35-50° C. under vacuum for 6 hours to remove residual isopropyl alcohol. The percentage yield of Losartan Potassium form I is 78%.

EXAMPLE 2

Under nitrogen atmosphere in a 2.0 liter flask, 125 ml. (20.00% w/v, 0.225 mole) solution of potassium tertiary butoxide in isoprolpyl alcohol is charged in methanol (725 ml). To this solution, 150 gm. of Trityl Losartan (0.225 mole) is added. The mixture is refluxed for 9 hours. The completion of reaction is monitored on TLC. After satisfactory completion, the reaction mass is concentrated to 50% and cooled to approximately −5° C. The reaction mass is filtered to separate the by-product from the reaction. After charcoalization of the filtrate, it is filtered through Celite. Residual methanol is distilled out completely and stripped out using isopropyl alcohol (75 ml. each) twice. Isopropyl alcohol (225 ml.) is charged, reflux for 1 hour, cooled and kept for 12 hours at 25-30° C.

The reaction mass is then cooled to 0-5° C. and filtered. The resulting product, Losartan Potassium is then washed with chilled isopropyl alcohol (45 ml.). The final product is dried at 35-50° C. under vacuum for 6 hours to remove residual isopropyl alcohol. The percentage yield of Losartan Potassium form I is 81%.

EXAMPLE 3

Under nitrogen atmosphere in a 2.0 liter flask, 15.60 gm (0.113 mole) anhydrous potassium carbonate is charged in methanol (725 ml). To this solution, 150 gm. of Trityl Losartan (0.225 mole) is added. The mixture is refluxed for 12 hours. The completion of reaction is monitored on TLC. After satisfactory completion, the reaction mass is concentrated to 50% and cooled to approximately −5° C. The reaction mass is filtered to separate the by-product from the reaction. After charcoalization of the filtrate, it is filtered through Celite. Residual methanol is distilled out completely and stripped out using isopropyl alcohol (75 ml each) twice. Isopropyl alcohol (225 ml) is charged, refluxed for 1 hour, cooled and kept for 12 hours at 25-30° C.

The reaction mass is then cooled to 0-5° C. and filtered. The resulting product, Losartan Potassium is then washed with chilled isopropyl alcohol (45 ml). The final product is dried at 35-50° C. under vacuum for 6 hours to remove residual isopropyl alcohol. The percentage yield of Losartan Potassium form I is 82%.

EXAMPLE 4

Under nitrogen atmosphere in a 2.0 liter flask, 15.60 gm (0.113 mole) anhydrous potassium carbonate is charged in methanol (725 ml). To this solution, 150 gm. of Trityl Losartan (0.225 mole) is added. The mixture is refluxed for 12 hours. The completion of reaction is monitored on TLC. After satisfactory completion, the reaction mass is concentrated to 50% and cooled to approximately −5° C. The reaction mass is filtered to separate the by-product from the reaction. After charcoalization of the filtrate, it is filtered through Celite. Residual methanol is distilled out completely and stripped out using tetrahydrofuran 150 ml twice. Again tetrahydrofuran 600 ml is charged and refluxed for 30 minutes and cooled to 25-30° C. and kept overnight.

The reaction mass is then chilled to 0-5° C. and filtered. The resulting product, Losartan Potassium is then washed with chilled tetrahydrofuran (45 ml). The final product is dried at 35-50° C. under vacuum for 6 hours to remove residual tetrahydrofuran. The percentage yield of Losartan Potassium form I is 90%.

The present invention is described above in connection with preferred or illustrative embodiments. These embodiments are not intended to be exhaustive or limiting of the invention. Rather the invention is intended to cover all alternatives, modifications and equivalents included within its scope, as defined by the appended claims.

We claim:
1. An improved process for the synthesis of losartan potassium comprising the steps of:
 (i) reacting approximately equimolar quantities of a potassium salt with trityl losartan in methanol;
 (ii) refluxing the reaction mixture to obtain a reaction mass comprising losartan potassium;
 (iii) monitoring the completion of reaction using TLC;
 (iv) concentrating the reaction mass to approximately 50%;
 (v) cooling the reaction mass to approximately −5° C.;
 (vi) distilling out the methanol from the reaction mass;
 (vii) stripping of methanol from the reaction mass using isopropyl alcohol;
 (viii) maintaining the reaction mass in secondary alcohol for approximately 12 hours at 25 to 30° C.;
 (ix) cooling the reaction mass to 0-5° C.;
 (x) filtering out losartan potassium;
 (xi) washing with chilled isopropyl alcohol; and
 (xii) drying the losartan potassium under vaccum.

2. The process for manufacturing losartan potassium as claimed in claim 1 wherein the tertiary alcohol is tertiary butanol.

3. The process for manufacturing losartan potassium as claimed in claim 1 wherein the secondary alcohol is isopropyl alcohol or isobutanol.

4. An improved process for manufacture of losartan potassium comprising the steps of:
 (a) reacting a mixture equimolar quantities of an anhydrous alkali metal salt in methanol with approximately 1 mole trityl losartan;
 (b) refluxing the reaction mixture for 10 to 15 hours; and
 (c) further procuring the reaction mixture as per process claimed in claim 1.

5. The process for manufacture of losartan potassium as claimed in claim 4 wherein anhydrous alkali metal salts are selected from the group consisting of anhydrous potassium carbonate, potassium bicarbonate, and potassium tertiary butoxide.

6. The process for manufacture of losartan potassium as claimed in claim 4 wherein the anhydrous alkali metal salt is anhydrous potassium carbonate.

7. The process for manufacturing of losartan potassium as claimed in claim 5, wherein the strength of the solution of potassium tertiary butoxide is 15 to 25% (w/v).

8. A process for manufacture of polymorph Form I of losartan potassium comprising:
 a. treating trityl losartan with equimolar quantity of anhydrous potassium salts in methanol;
 b. refluxing the resultant mixture for a period of 7-12 hours;
 c. concentrating methanol to half volume;
 d. filtering triphenyl methyl methyl ether;
 e. concentrating the methanol mixture to 50%;
 f. removing residual solvent using solvents;
 g. keeping the mass at temperature 25-30° C. for aging the crystal growth for a period of 10 to 15 hours;
 h. chilling the reaction mass to a temperature of 0-5° C. to precipitate the crystals of polymorph form I; and
 i. filtering the precipitated crystals to yield polymorph Form I.

9. A process for manufacture of polymorph Form I of losartan potassium comprising: a) dissolving losartan potassium obtained after detritylation, in tetrahydrofuran or its mixture thereof with other solvents at reflux, b) cooling to a temperature of 25-30° C., c) aging the crystal at this temperature for a period of 7-13 hours, and d) cooling the mass to a temperature of 0-5° C. to effect complete crystallization.

10. The process for manufacture of polymorph Form I of Losartan potassium according to claim 9 wherein the Losartan potassium used for dissolution in tetrahydrofuran is made by a process comprising the steps of:
- (i) reacting approximately equimolar quantities of a potassium salt with trityl losartan in methanol;
- (ii) refluxing the reaction mixture to obtain a reaction mass comprising losartan potassium;
- (iii) monitoring the completion of reaction using TLC;
- (iv) concentrating the reaction mass to approximately 50%;
- (v) cooling the reaction mass to approximately −5° C.;
- (vi) distilling out the methanol from the reaction mass;
- (vii) stripping of methanol from the reaction mass using isopropyl alcohol;
- (viii) maintaining the reaction mass in secondary alcohol for approximately 12 hours at 25 to 30° C.;
- (ix) cooling the reaction mass to 0-5° C.;
- (x) filtering out losartan potassium;
- (xi) washing with chilled isopropyl alcohol; and
- (xii) drying the losartan potassium under vaccum.

11. The process for manufacturing losartan potassium as claimed in claim 1 wherein the potassium salt is potassium tertiary butoxide as a solution in a secondary or tertiary alcohol.

12. The process for manufacture of polymorph Form I of losartan potassium according to claim 8 wherein the solvent in step f) is isopropyl alcohol, tetrahydrofuran, or mixture thereof.

13. The process for manufacture of polymorph Form I of Losartan potassium according to claim 9 wherein the tetrahydrofuran in step a) is mixed with isopropyl alcohol.

* * * * *